(12) United States Patent
Stewart, III

(10) Patent No.: US 6,453,919 B2
(45) Date of Patent: Sep. 24, 2002

(54) CONTACT LENS CLEANING SOLUTION OVERFLOW COLLECTOR

(76) Inventor: Kenneth G. Stewart, III, P.O. Box 1117, Sarasota, FL (US) 34230

( * ) Notice: Subject to any disclaimer, the term of this patent is extended or adjusted under 35 U.S.C. 154(b) by 84 days.

(21) Appl. No.: 09/747,954

(22) Filed: Dec. 27, 2000

Related U.S. Application Data

(60) Provisional application No. 60/171,660, filed on Dec. 27, 1999.

(51) Int. Cl.7 .................................................. B08B 3/04
(52) U.S. Cl. ........................ 134/201; 134/901; 206/5.1; 422/301
(58) Field of Search ................................ 134/901, 201; 206/5.1; 422/301

(56) References Cited

U.S. PATENT DOCUMENTS 5,275,784 A * 1/1994 Perlaky .................. 134/901 X
5,520,277 A * 5/1996 Alvord ................... 134/901 X

* cited by examiner

Primary Examiner—Philip Coe
(74) Attorney, Agent, or Firm—Barnes & Thornburg

(57) ABSTRACT

The invention provides for an anti-drip feature for the common contact lens cleaning cup so as to avoid spillage of cleaning solution by providing an overflow container which attaches to the lens cleaning cup to catch spillage.

18 Claims, 2 Drawing Sheets

CONTACT LENS CLEANING SOLUTION OVERFLOW COLLECTOR

This application claims priority benefit from provisional application No. 60/171,660 filed Dec. 27, 1999.

BACKGROUND AND SUMMARY OF THE INVENTION

The invention relates to a spillage collector for a contact lens cleaning system. In particular, the invention envisions the placement of a contact lens cleaning system container in a collector container during lens cleaning so that leakage from the contact cleaning system is collected in the container.

In a known lens cleaning system such as the AOSEPT® system of CIBA VISION®, a Novartis Company, a plastic container is provided with an internal lens basket into which a lens is placed for cleaning. After placement of the lens into the basket, disinfectant is poured into the container and the lens basket is inserted into the container. Lens cleaning occurs by the disinfectant which due to a chemical reaction with a platinum-coated neutralizer attached to the bottom of the lens basket causes bubbling of the disinfectant that cleans proteins and other debris from the lens in the basket. The cleaning process normally takes place overnight, i.e. the lens is placed into the container at bedtime and left to be cleaned over night. The plastic container has a cap to contain the disinfectant and the cap is provided with a weep hole to allow release of gasses from the chemical reaction. Usually, some of the bubbling disinfectant passes out of the plastic container through the weep hole in the cap and runs down the outer side of the plastic container onto the surface on which the container is set.

The invention concerns itself with a collector to accept the disinfectant that is discharged through the weep hole in the cap for the plastic container so that the surface on which the plastic container is placed is not contaminated by the disinfectant coming out of the weep hole.

Other objects, advantages and novel features of the present invention will become apparent from the following detailed description of the invention when considered in conjunction with the accompanying drawings.

DESCRIPTION OF THE DRAWINGS

Figure 1:
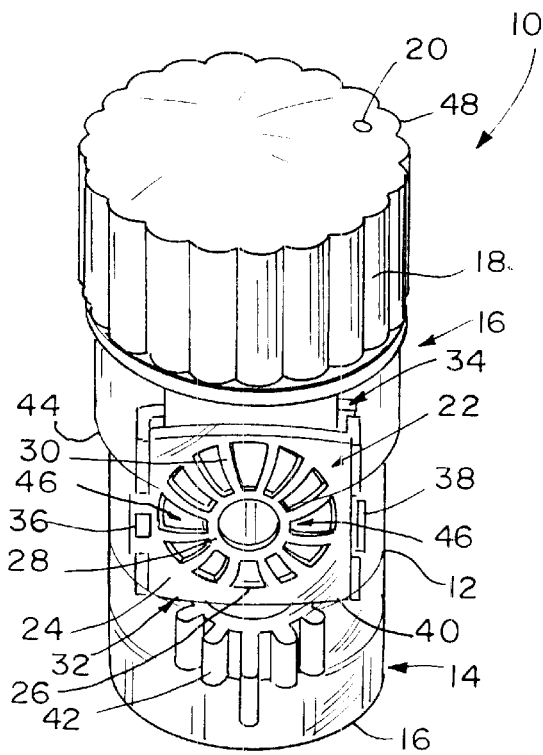
FIG. 1 shows the prior art lens disinfectant plastic lens cleaning container AOSEPT® system.

FIG. 1 shows the well-known AOSEPT® contact lens cleaning system 10 which includes a hollow plastic container 12 with a base portion 14, a bottom 16, top portion 16 closed by a cap 18. The cap 18 is provided with a weep hole 20 which provides for an opening into the plastic container 12. Fixedly attached to the underside of the cap 18 is a plastic contact lens basket 22. The lens basket 22 has a mesh front 32 and back 34 defined by an outer solid portion 24, with a circular opening 26. The opening 26 is provided with an inner circular ring 28 held to the outer solid portion 24 by a plurality of radial spokes 30. The front 32 is coupled to the back 34 by hinge 36 and is held closed by a snap clasp 38. Attached to the lens basket at its bottom 40 is a platinum-coated neutralizer 42. The top portion 16 of the plastic container 12 has an enlarged outer diameter to provide a visual indicator disinfectant fill line 44.

In use the cap 18 is unscrewed from the plastic container 12. The lens basket 22 clasp 38 is opened by pivoting the front 32 about hinge 36 and the contact lens to be cleaned is set on a lens pedestal 46 located within the lens basket 22 and attached to the back 34 of the lens basket 22. The front 32 is then pivoted shut and the clasp 38 snapped over the front 32 to hold the basket closed. The plastic container is then filled with disinfectant up to the fill line 44. The cap 18 with the lens basket 22 inserted into the plastic container 12 is screwed onto the container 12. The plastic container 12 bottom 16 in then rested on a flat surface. As the disinfectant chemically reacts with the platinum-coated neutralizer 42 it foams or bubbles. This agitation of the disinfectant through the openings 46 between the spokes 30 and the interior of inner circle 28 washes the contact lens located within the lens basket 22. Bubbling of the disinfectant causes a seepage of disinfectant through weep hole 20 which can run over the edge 48 of the cap 18 and down the outer side of the plastic container 12 to contaminate the surface on which the plastic container 12 is set.

Figure 5:
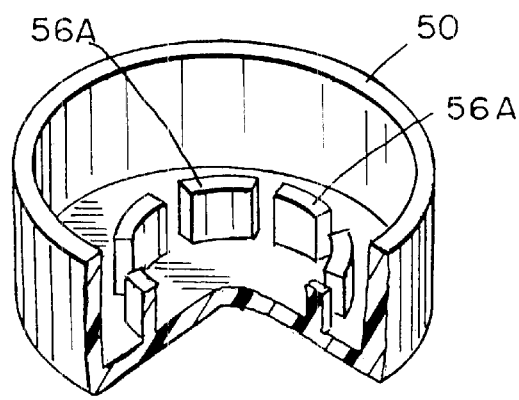
FIG. 5 shows a modified embodiment of the connection of FIG. 3 wherein the inner stabilizing wall is formed by a series of arc wall segments.

To avoid contamination of the supporting surface, the invention provides for an overflow cup 50 (FIG. 2) preferably attached to the bottom of the plastic container 12. The overflow cup 50 has a bottom 52 and a circular outer wall 54 extending upwardly from an outer edge 52 of the bottom 52. The diameter of the bottom 52 is larger than that of the outer diameter of cap 18, so that disinfectant seeping out of the weep hole 20 can run down the side of the cap 18 and plastic container 12 into the cup 50 where it is collected. Internally of the cup 50 (see FIG. 3) is an inner circular stabilizing ring wall 56 extending upwardly that is press fit into a hollow 58 formed by a lower skirt portion 60 of the outer bottom surface of the plastic container 12. While FIG. 3 shows the inner wall 56 to be a complete ring, it could be formed by a series of arc wall segments 56a (FIG. 5) for ease of insertion into the cavity 58. Ideally, the inner stabilizer ring wall 56 is press fit into the cavity to insure that the cup 50 is not disengaged from the plastic container 12. While the inner stabilizer ring wall 56 is shown fitting internally into the cavity 58 of the plastic container 12 in FIG. 3, it could be external to the skirt portion 60. Here also there should be a press fit between the inner stabilizer ring wall 56 and the outer wall of skirt 60 to insure attachment of the cup 50 to the plastic container 12.

Figure 2:
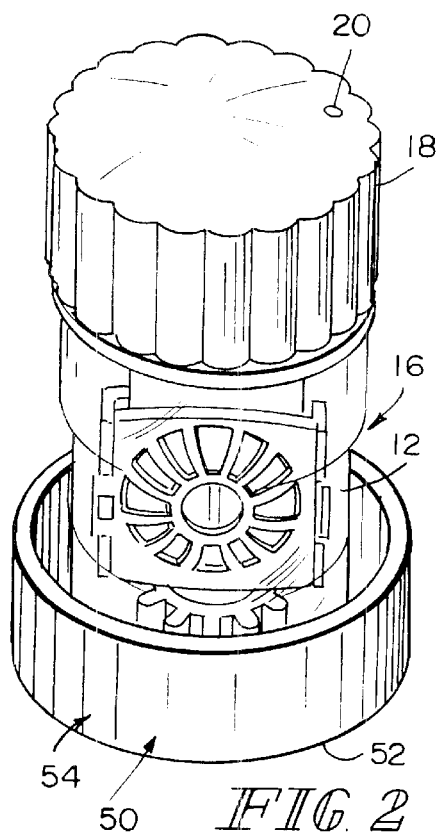
FIG. 2 shows a first embodiment of the collector system wherein the plastic AOSEPT® lens cleaning container is placed into a collector.
Figure 3:
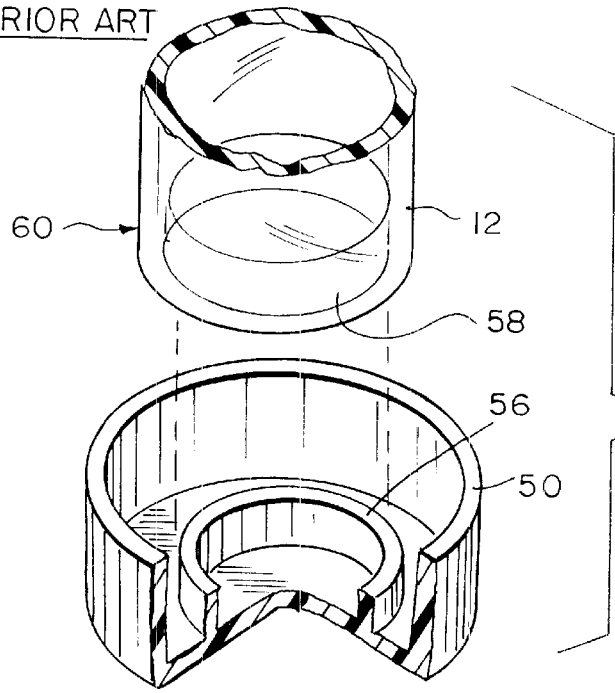
FIG. 3 shows schematically and partially in section the connection between the collector of FIG. 2 and the plastic lens container.
Figure 4:
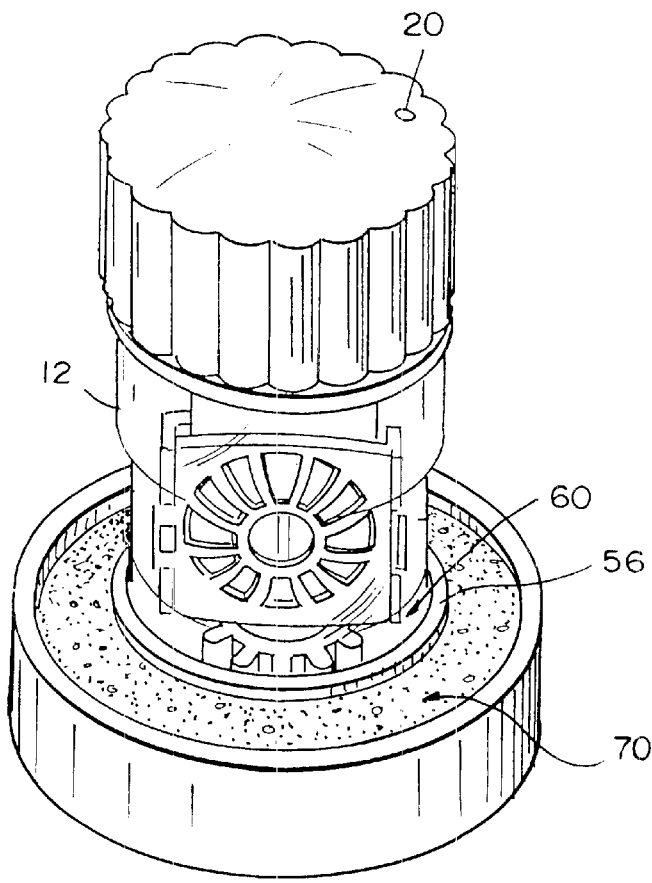
FIG. 4 shows a second embodiment of a collector for a lens cleaning system.

FIG. 4 shows a modification of the cup of FIG. 2. In this modification the limit stabilizer ring inner wall 56 is located outside of the skirt portion 60 of the plastic container 12. Surrounding the inner stabilizer ring wall is a sponge 70 to collect the overflow of containments out of the weep hole 20. The sponge 70 can be loose about the inner stabilizer ring wall 56 or press fit or fixedly secured about the outer edge of the inner stabilizer ring wall 56. Having the sponge loose allows for easier cleaning and replacement, since the sponge can be removed from the cup 50 for washing.

What is claimed is:

1. An anti-spillage system for contact lens cleaning comprising:

a lens cup with an open top to allow filling of the cup with contact lens solution, a cap to close the lens cup top, an lens holder mounted in the lens cup to be immersed in contact lens cleaning solution, an overflow container connected to a bottom portion of the lens cup, the overflow container provided with an inner wall that is spaced apart from an outer wall of the container and with a bottom floor extended between bottom portions of the inner and outer wall to define a cavity between the walls for collection of contact lens solution leaking from the lens cup, and wherein the inner wall of the overflow container has a configuration similar to the configuration of a bottom of the lens cup so that the overflow container and lens cup can nest together.

2. The anti-spillage system of claim 1 wherein the inner wall configuration is slightly larger than the configuration of the bottom of the lens cap so that the inner wall snugly fits about the exterior of the lens cap bottom.

3. The anti-spillage system of claim 2 wherein the configuration of the inner wall of the overflow container is composed of spaced segments the totality of which are similar to the configuration of the bottom of the lens cup to allow flexure to the inner wall for a tight nested fit.

4. The anti-spillage system of claim 3 wherein a sponge is located within the cavity to absorb lens solution in the cavity.

5. The anti-spillage system of claim 4 wherein the sponge loosely fits within the cavity.

6. The anti-spillage system of claim 2 wherein a sponge is located within the cavity to absorb lens solution in the cavity.

7. The anti-spillage system of claim 6 wherein the sponge loosely fits within the cavity.

8. The anti-spillage system of claim 1 wherein the inner wall configuration is slightly smaller than the configuration of the bottom of the lens cap so that the inner wall snugly fits about an interior recess in the lens cap bottom.

9. The anti-spillage system of claim 8 wherein the configuration of the inner wall of the overflow container is composed of spaced segments the totality of which are similar to the configuration of the bottom of the lens cup to allow flexure to the inner wall for a tight nested fit.

10. The anti-spillage system of claim 9 wherein a sponge is located within the cavity to absorb lens solution in the cavity.

11. The anti-spillage system of claim 10 wherein the sponge loosely fits within the cavity.

12. The anti-spillage system of claim 8 wherein a sponge is located within the cavity to absorb lens solution in the cavity.

13. The anti-spillage system of claim 12 wherein the sponge loosely fits within the cavity.

14. The anti-spillage system of claim 1 wherein the configuration of the inner wall of the overflow container is composed of spaced segments the totality of which are similar to the configuration of the bottom of the lens cup to allow flexure to the inner wall for a tight nested fit.

15. The anti-spillage system of claim 14 wherein a sponge is located within the cavity to absorb lens solution in the cavity.

16. The anti-spillage system of claim 15 wherein the sponge loosely fits within the cavity.

17. The anti-spillage system of claim 1 wherein a sponge is located within the cavity to absorb lens solution in the cavity.

18. The anti-spillage system of claim 17 wherein the sponge loosely fits within the cavity.

* * * * *